(12) United States Patent
Höök et al.

(10) Patent No.: US 9,606,047 B2
(45) Date of Patent: Mar. 28, 2017

(54) WAVEGUIDE STRUCTURE

(71) Applicant: GOTHENBURG SENSOR DEVICES AB, Göteborg (SE)

(72) Inventors: Fredrik Höök, Alingsås (SE); Björn Agnarsson, Partille (SE); Anders Lundgren, Varberg (SE); Anders Gunnarsson, Göteborg (SE); Marta Bally, Göteborg (SE); Lisa Simonsson Nyström, Lerum (SE)

(73) Assignee: GOTHENBURG SENSOR DEVICES AB (SE)

( * ) Notice: Subject to any disclaimer, the term of this patent is extended or adjusted under 35 U.S.C. 154(b) by 0 days.

(21) Appl. No.: 14/901,639

(22) PCT Filed: Jun. 26, 2014

(86) PCT No.: PCT/EP2014/063491
§ 371 (c)(1),
(2) Date: Dec. 28, 2015

(87) PCT Pub. No.: WO2014/207089
PCT Pub. Date: Dec. 31, 2014

(65) Prior Publication Data
US 2016/0153888 A1    Jun. 2, 2016

(30) Foreign Application Priority Data

Jun. 28, 2013 (SE) ...................... 1350790

(51) Int. Cl.
*G01N 21/64* (2006.01)
*G01N 21/01* (2006.01)
(Continued)

(52) U.S. Cl.
CPC ........... *G01N 21/01* (2013.01); *G01N 21/648* (2013.01); *G01N 21/6428* (2013.01);
(Continued)

(58) Field of Classification Search
CPC ............... G01N 21/01; G01N 21/6428; G01N 21/6458; G01N 21/648; G01N 2201/06113;
(Continued)

(56) References Cited

U.S. PATENT DOCUMENTS

| | | |
|---|---|---|
| 5,857,039 A | 1/1999 | Bosc et al. |
| 6,753,188 B2 | 6/2004 | Perkins et al. |
| 2011/0306143 A1 | 12/2011 | Chiou et al. |

FOREIGN PATENT DOCUMENTS

WO    2007077218 A1    7/2007

OTHER PUBLICATIONS

Agnarsson et al: "Evanescent-wave fluorescence microscopy using symmetric planar waveguides"; Optics Express, vol. 17, No. 7, Mar. 30, 2009, pp. 5075-5082.
(Continued)

*Primary Examiner* — Ryan Lepisto
*Assistant Examiner* — Erin Chiem
(74) *Attorney, Agent, or Firm* — Lerner, David, Littenberg, Krumholz & Mentlik, LLP

(57) ABSTRACT

A waveguide structure for evanescent wave microscopy and/or spectroscopy, comprising an optically transparent core layer, a lower dielectric cladding layer and an upper dielectric cladding layer arranged on opposite sides of the core layer. The core layer has a refractive index higher than the refractive indices of the cladding layers. The upper cladding layer is made of an organic material. A sample well is arranged on an upper surface of the core layer formed by a cavity in the upper cladding layer, the sample well being adapted to contain a sample medium with one or more sample objects. The core layer is made of a first dielectric inorganic material, and the upper cladding layer has a refractive index which closely matches the refractive index
(Continued)

of the sample medium. A method for manufacturing such waveguide structure, and a measurement system comprising the waveguide structure are also disclosed.

18 Claims, 8 Drawing Sheets

(51) Int. Cl.
  *G02B 6/122* (2006.01)
  *G02B 21/16* (2006.01)
  *G02B 6/12* (2006.01)
(52) U.S. Cl.
  CPC ....... *G01N 21/6458* (2013.01); *G02B 6/1221* (2013.01); *G02B 21/16* (2013.01); *G01N 2201/061* (2013.01); *G01N 2201/062* (2013.01); *G01N 2201/06113* (2013.01); *G01N 2201/08* (2013.01); *G02B 2006/12176* (2013.01)
(58) Field of Classification Search
  CPC ......... G01N 2201/08; G01N 2201/062; G01N 2201/061; G02B 21/16; G02B 6/1221; G02B 2006/12176
  See application file for complete search history.

(56) References Cited

OTHER PUBLICATIONS

Agnarsson et al.; "Fabrication of planar polymer waveguides for evanescent-wave sensing in aqueous environments"; Microelectronic Engineering, 2010; vol. 87, No. 1, pp. 56-61.
Halldorsson et al.: "High index contrast polymer waveguide platform for integrated biophotonics", 2010 OSA, vol. 18, No. 15, pp. 16217-16226.
Sharma et al.; Control of birefringence using polymer as cladding layer in optical planar waveguides; Optik—Int. Journal for Light and Electron Optics, 9//, 2010; vol. 121, No. 17, pp. 1610-1613.
International Search Report and Written Opinion for Application No. PCT/EP2014/063491 dated Oct. 14, 2014.
Bosc et al.; Hybrid silica-polymer structure for integrated optical waveguides with new potentialities. Materials Science and Engineering; 1999, vol. 57, No. 2, pp. 155-160.

WAVEGUIDE STRUCTURE

CROSS-REFERENCE TO RELATED APPLICATIONS

The present application is a national phase entry under 35 U.S.C §371 of International Application No. PCT/EP2014/063491 filed Jun. 26, 2014, which claims priority from Sweden Application No. 1350790-0 filed Jun. 28, 2013, all of which are hereby incorporated herein by reference.

TECHNICAL FIELD

Waveguide structures, especially for evanescent wave microscopy and/or spectroscopy, and methods for manufacturing such waveguide structures. Measurement systems comprising such waveguide structures are also disclosed.

BACKGROUND

Total internal reflection fluorescence (TIRF) microscopy is a commercially available technology for detection and visual monitoring of fluorescently labeled nano- and microscopic objects, such as cells, nanoparticles, lipid vesicles, molecules etc., in the close vicinity of or on surfaces.

In cell and molecular biology, different molecular events occurring in or close to cellular surfaces such as cell adhesion, binding to cells of hormones, secretion of neurotransmitters, membrane dynamics and cellular interaction with inorganic surfaces have been studied with conventional fluorescence microscopes. However, fluorophores that are bound to the specimen and those in the surrounding medium often exist in an equilibrium state. When these molecules are excited and detected with a conventional fluorescence microscope, the resulting fluorescence from those fluorophores bound to the cellular and/or inorganic surface is often overwhelmed by the background fluorescence due to the much larger number of non-bound molecules.

The concept of using total internal reflection to illuminate cells or other small-scale fluorescently labelled objects contacting the surface of a transparent material such as e.g. glass has been known for several decades. A TIRF microscope uses an evanescent wave to selectively illuminate and excite fluorophores in a restricted region of the specimen immediately adjacent to a glass-water interface. The evanescent wave is generated only when the incident light is totally internally reflected at the glass-water interface. The evanescent electromagnetic field decays exponentially from the interface, and thus penetrates to a depth of only approximately 100 nm into the sample medium. Thus the TIRF microscope enables a selective visualization of surface regions such as the basal plasma membrane (which are about 7.5 nm thick) of cells. TIRF can also be used to observe the fluorescence of single fluorescent nanoscale objects as well as single molecules, making it an important tool of biophysics and quantitative biology.

Examples of TIRF-related techniques are given in U.S. Pat. No. 6,753,188 and WO2007/077218.

A potential drawback with the TIRF technology is that it typically requires labelling of molecules under investigation, which may affect the material, e.g. live cells or nanoparticles, to be studied. Furthermore, from a practical point of view, fluorescence labelling is not always straight forward to implement.

It is thus of interest to provide a technique capable of doing in principle the same thing as TIRF but that does not require labelling. It is also of interest to provide a technique that is more sensitive than TIRF, without being too complicated and costly.

SUMMARY

A waveguide structure for evanescent wave microscopy and/or spectroscopy is presented. The waveguide structure comprises an optically transparent core layer, a first, lower, dielectric cladding layer and a second, upper, dielectric cladding layer arranged on opposite sides of the core layer. The core layer has a refractive index higher than the refractive indices of the cladding layers.

A sample well is arranged on an upper surface of the core layer formed by a cavity in the second cladding layer. The sample well is adapted to contain a sample comprising a sample medium with one or more sample objects. Thereby, when used in a measurement set-up, for example as described below, the light incoupling region may be separated from the sample solution. Thereby, stray light in the liquid may be minimized. The upper cladding layer may also protect the parts of the waveguide not used for excitation from contamination. Such contamination might result in uneven light distribution within the core layer.

At least the second, upper, cladding layer is made of an organic material. The second cladding layer is selected such that is has a refractive index which closely matches the refractive index of the sample medium of the sample intended to be probed.

A number of different media may be used as sample medium. For example, water is commonly used, especially when studying biological samples. Other examples may be emulsions, oil, ionic liquids, ethanol or methanol.

By matching the refractive index of the organic cladding part of the structure to that of the sample medium a high signal to background ratio may be achieved, when detecting scattering signals. When the light enters the well of the waveguide structure, stray light scattering originating from the cladding to well interface is greatly reduced by index matching the upper cladding layer with that of the sample medium. Reducing stray light scattering allows monitoring nanoparticles without the need of fluorescence labelling.

The core layer is made of a first dielectric inorganic material. An inorganic core layer may be advantageous, since it may increase the possibility of surface functionalization. An inorganic core layer is especially advantageous in the field of cell biology and molecular biology described above. However, due to e.g. difficulties of manufacturing hybride waveguides, waveguide structures for evanescence measurements with organic cladding have previously been all-organic structures. However, some organic materials conventionally used as core layer have been shown to be disadvantageous when studying biological samples, as will be described below.

When light is guided into the waveguide structure, an evanescent wave is formed at the outer boundaries of the core layer. The penetration depth of the evanescent wave into the sample well may be accurately defined, by the specific material properties and thicknesses of the different layers. Sample objects located within the penetration depth of the evanescent wave will interact with the confined light and may either absorb, absorb and re-emit, or scatter the light. Such scattering and/or absorbance may result in for example fluorescence or emittance of optical radiation which can be detected, and used for microscopic and/or spectroscopic studies of the sample objects. The waveguide structure may therefore be used for evanescent wave microscopy and/or spectroscopy measurements of a sample positioned within the sample well. If the sample objects under examination are fluorescent, fluorescence and scattering of evanescent light may occur more or less simultaneously within the sample. Measurement systems for the simultaneous measurement of fluorescence light signals and scattering light signals are described below.

The second cladding layer may be made of a fluorinated polymer.

Also the first, lower, cladding layer may be made of an organic material, preferably a fluorinated polymer.

The root means square roughness of the upper surface of the core layer may be configured such that it does not exceed 1 nm.

The second cladding layer may have a refractive index within the interval 1.30-1.36. Thereby, the refractive index of the second cladding layer may be matched to that of water, which may be used as sample medium when measuring biological samples.

The first cladding layer may have a refractive index lower than, or equal to, the refractive index of the second cladding layer. This may influence both the incoupling of light as well as penetration depth of the evanescent part of the fundamental mode supported by the waveguide structure, in a way which may be advantageous in certain situations. Alternatively, the first cladding layer may have a refractive index higher than the second cladding layer.

The properties of the first and second cladding layers may be similar such as to define a symmetric cladding environment for the core layer. A symmetric waveguide structure may simplify incoupling of light and increase the penetration depth of the evanescent field.

The core layer may be made of $SiO_2$, $Si_xN_y$, $Al_2O_3$ or $TiO_2$. Alternatively, the core layer may be made of other optically transparent materials. The core layer may be formed such that the waveguide structure supports a single or multiple wavelengths within, or throughout, a wavelength spectrum ranging from UV, via visible and to the near IR-region.

The core layer may have been spin-coated onto the first cladding layer. For example, the core layer may be formed by a spin on glass. The spin on glass may be inorganic silicate based or organic polysiloxane based. When based on organic polysiloxane, $SiO_2$ nanoparticles may be mixed in an organic solution containing methyl, ethyl or phenyl groups. Alternatively or additionally, the organic solution may contain polymer-bound hydroxyl groups.

Alternatively, the core layer may have been deposited onto the first cladding layer. Deposition should be performed at a temperature below the first cladding layer. Thereby, delamination of the layers and/or crack-formations within one or both layers may be avoided.

The first cladding layer may be arranged on a substrate that supports the waveguide structure. Preferably, the substrate may be glass or a Si-wafer, or a polymer, such as polyimide wafer. Alternatively, a mirror or a metal mat be used as substrate.

The waveguide may be a single mode waveguide structure.

The surface of the core layer within the sample well may be coated with an electrically conductive film having an optical transparency. Examples of such films are graphene, conductive polymers, indium tin oxide or a thin metal layer. Thereby, it may be possible to perform also electrochemical measurements of the sample. Preferably, electrochemical measurements may be performed simultaneously with microscopic and/or spectroscopic measurements. The surface of the core layer within the sample well may also be coated with a thin sheet of metallic layer either continuous or structured to induce plasmonic effects.

A method is presented for manufacturing a waveguide structure comprising:
  an optically transparent core layer made of a first dielectric inorganic material,
  a first, lower, dielectric cladding layer and a second, upper, dielectric cladding layer arranged on opposite sides of the core layer, wherein the core layer has a refractive index higher than the refractive indices of the cladding layers, and wherein each of the first and second cladding layers is made of an organic material,
  a sample well arranged on an upper surface of the core layer formed by a cut-out/open cavity in the second cladding layer, the sample well being adapted to contain a sample comprising a sample medium with one or more sample objects. Especially, a waveguide structure for evanescent microscopy and/or spectroscopy measurements may be manufactured by the method. For example, waveguide structures according to any of the examples described above may be manufactured by the method.

The method comprises the steps of:
i) applying the first cladding layer onto a substrate;
ii) applying the core layer onto the first cladding layer at a temperature that is lower than a glass-transition temperature of the material of the first cladding layer; and
iii) applying the second cladding material onto the core layer at a temperature that is lower than a glass-transition temperature of the material of both the first cladding layer and the second cladding layer;
iv) forming a sample well on an upper surface of the core layer by removing material from the second cladding layer and forming an open cavity therein.

By applying the second cladding material to the core layer at a temperature lower than the glass-transition temperature of the material of the first and second cladding layers thermally induced defects in the waveguide structure may be avoided or at least minimized. Especially, cracks in the cladding layers may be avoided, as well as deformation of the different layers and detachment of the different layers from each other.

The method may further comprise one or several of the following steps:
  priming an upper surface of the substrate to improve adhesion properties before applying the first cladding layer;
  spin-coating the first cladding layer onto the substrate;
  curing or hardening the first cladding layer after application onto the substrate;
  decreasing hydrophobicity of an upper surface of the first cladding layer before applying the core layer, preferably by applying, and subsequently removing, a thin metallic layer onto the first cladding layer;
  using a fluorinated polymer as the material forming the first cladding layer;
  spin-coating the core layer onto the first cladding layer;
  spin-coating the second cladding layer onto the core layer;
  using a fluorinated polymer as the material forming the second cladding layer;
  curing or hardening the second cladding layer after application onto the core layer at a temperature which is lower than the temperature at which the first cladding layer was cured;
  decreasing hydrophobicity of an upper surface of the second cladding layer before forming an etch mask thereon, preferably by applying, and subsequently removing, a thin metallic layer onto the second cladding layer;

forming an etch mask onto the second cladding layer, the etch mask defining the size of the sample well;

etching through an exposed part of the second cladding layer to form the sample well;

etching through an exposed part of the second cladding layer to form the sample well, whereby the core layer functions as an etch stop layer, such that no additional etch stop layer is used; and/or coating the surface of the core layer within the sample well with an electrically conductive film having an optical transparency.

For example, the surface of the core layer within the sample well may be coated with a thin layer of, e.g., graphene, conductive polymers, indium tin oxide or a thin metal layer.

The core layer may be applied by spin coating a spin-on glass (SOG) onto the first cladding layer and curing or hardening the SOG layer at a temperature that does not exceed the glass transition temperature of the first cladding layer for a time of at least approximately 24 hours. Preferably, curing may take place at a temperature substantially equal to the glass transition temperature of the first cladding layer for a time equal to or exceeding 24 hours, to thereby form a $SiO_2$ core layer.

The core layer may be formed by any type of deposition technique or by spin coating of sol-gel materials onto the first cladding layer. For example, $Si_xN_y$, $Al_2O_3$ or $TiO_2$ may be applied onto the first cladding layer. Sol-gel materials are solid materials dissolved in a solution, which may be spin coated onto a surface such as to form solid films or other forms of solid material. The process of spin coating or depositing should be performed at a temperature below the glass-transition temperature of the first cladding layer. Thereby, delamination of the layers and/or crack-formations within one or both layers may be avoided.

A measurement system is disclosed. The measurement system may comprise:

a waveguide structure as described above, at least one light source configured to direct light into the core layer of the waveguide structure towards the sample well, and a detector arrangement configured to detect light emitted from a sample comprising one or more sample objects in a sample medium placed in the sample well.

The sample well may be adapted for housing the sample to be probed by the measurement system. The sample well may be configured for containing a sample medium comprising one or more sample objects. The refractive index of the second, upper, cladding layer may be chosen such that it deviates from the refractive index of the sample medium by 0.03 or less.

The at least one light source may be butt-coupled to the core layer of the waveguide structure.

The at least one light source may be a laser or any other single transverse mode light source.

The detector arrangement may comprise a first detector arranged to measure fluorescence signals emanating from the sample objects and a second detector arranged to measure scattering signals from the sample objects. The detector arrangement may be adapted such that fluorescence signals and scattering signals can be detected simultaneously.

A first filter may be arranged to filter out scattering signals such that only fluorescence signals reach the first detector. A second filter may be arranged to filter out fluorescence signals such that only scattering signals reach the second detector.

A first objective may be arranged between the waveguide structure and the first filter. A second objective may be arranged between the waveguide structure and the second filter.

A dichroic mirror may be arranged between the wave guide structure and the first and second detectors. The dichroic mirror may be arranged to separate fluorescence signals and scattering signals emanating from the sample objects such as to direct fluorescence signals toward the first detector and scattering signals toward the second detector. A first objective may be arranged between the waveguide structure and the dichroic mirror.

The use of a measurement system as described above for detecting adsorption of metal, dielectric or fluorescently labelled nanoparticles to the core layer of the waveguide structure is disclosed.

The waveguide structure may be based on dielectric hybrid inorganic-organic symmetric planar waveguide structure. A symmetric waveguide is a waveguide form where the core layer is placed in between upper- and lower cladding layers with similar optical properties, i.e. same or similar refractive indices. In a planar waveguide, most of the light is confined to the core layer of the structure. However, a small part of the confined light extends into the surrounding cladding layers as an evanescent wave, which has a finite penetration depth. If an object is placed within the penetration depth of the evanescent wave in the cladding, it will interact with the confined light and either absorb, absorb and re-emit, or scatter the light. The emitted or scattered light can be detected using a light sensitive device, for example a camera or a spectrometer. This principle is similar to the one used in TIRF microscopy and ensures high signal to background ratio since only objects within the reach of the evanescent field, and not outside it, will be effected.

The preferred symmetry of the structure (essentially identical optical properties of the upper and lower cladding layers) ensures effective in-coupling of light using a simple butt-coupling method that eliminates the need for sophisticated grating- or prism in-coupling schemes. The symmetry also ensures that there the core layer has no cut-off thickness for the fundamental mode supported by the waveguide structure, which means that the structure can always support the fundamental modes of light over a broad wavelength spectrum. The same waveguide structure can thus support a single wavelength as well as multiwavelength light. The waveguide structure may support wavelength in the visible region of the spectrum, and/or in the UV part and/or the near-IR part of the spectrum. Preferably, the waveguide structure may be adapted to support the fundamental modes of light over a wavelength spectrum spanning from the UV region to the near-IR region.

The core layer of the waveguide may be formed by inorganic $SiO_2$ (or other suitable inorganic dielectric materials). $SiO_2$ is the preferred material of choice for carrying out surface based bio-analytical sensing and imaging experiments.

The waveguide structures as disclosed herein allow for simple TIR-like illumination that can be used together with any standard (inverted or upright) microscope.

Compared to TIRF microscopes, the waveguide structure according to the present disclosure has the benefits that it allows for: a) both microscopic and macroscopic illumination areas, b) simple multicolour excitation, c) tailoring of penetration depths by varying the core layer thickness or the refractive index of the core layer, and d) simultaneous observations of scattering and/or emitted signals, such as fluorescence or infrared signals, from the same or different regions of the substrate.

The waveguide structures and systems described herein provide for label-free detection and monitoring of nano- and microscopic objects on surfaces, such as dielectrics (e.g. lipid vesicles, biological cells, bacteria, or viruses or polymers), metallic (e.g. Au or Ag) or metal-oxide (e.g. $TiO_2$ or $SiO_2$) or semiconducting (e.g. quantum dots) or magnetic particles. The possibility to monitor nanoscale objects on surfaces can also be used for chemical sensing with single-molecule sensitivity.

High signal to background ratios are ensured thanks to waveguide-based evanescent wave-excitation in a small volume adjacent to the interface of probing part of the waveguide.

Thanks to the refractive index matching of the upper cladding layer to that of the sample medium and due to the choice of material of the core and cladding respectively, an improved sensitivity is obtained compared to conventional waveguide designs. This is further described below.

An additional advantage of the invention is that it provides for a simple and sensitive way of measuring scattered signals from micro- and nanoscopic objects. The concept described herein does not require any sophisticated devices, is compatible with standard microscopes and can be assembled into a stand-alone unit. Simplicity is a key factor here, since it converts to low production price.

The Hybrid Organic-Inorganic Waveguide Platform

Waveguides are conventionally either all-inorganic (insulators, semiconducting materials and/or metals) or all-organic (polymers, conductive polymers and/or biologically produced substances). There are several good reasons for fabricating waveguides using organic materials, for example polymers, instead of the more conventional inorganic materials. One is that polymers generally have a broader range of material properties compared to their inorganic counterparts. This includes a wider range of possible refractive indices, thermal coefficients, elastic coefficients, etching procedures, easily produced layer thicknesses, electrical properties etc. This makes tailoring of the optical and structural properties to specific needs easier than for inorganic materials. Polymers can furthermore be directly spin-coated on each other making the need for sophisticated deposition machinery unnecessary. On the other hand, inorganic materials also offer certain advantages compared with organic materials. They can for example usually be fabricated in a more controlled manner, with higher material- and structural purity then organic materials. They also tend to be more structurally robust and chemically inert. It is typically also easier to chemically modify their surface properties, which often offers advantages in bioanalytical contexts. The methods and devices used in the ever-growing semiconductor industry can furthermore be directly applied for making inorganic waveguide structures. In some cases inorganic materials can be mixed into solutions of organic materials and spin-coated onto a substrate in a similar manner as polymers. This is the case for spin-on-glass (SOG), which is an organic solvent mixed with $SiO_2$ nanoparticles. Upon heating the organic compounds evaporate, leaving only the $SiO_2$ particles behind to form the inorganic film with similar properties as evaporated, sputtered or chemical vapour deposited $SiO_2$.

The hybrid organic-inorganic waveguide structures as disclosed herein combine "the best of both worlds". However, the fabrication of such a structure is not straightforward due to inherent material property differences between the two types of materials. For instance the difference in thermal expansion coefficient between polymers and inorganic solid materials is usually large, meaning that layered structures containing both material types tend to form cracks during processing. In the disclosed method, the processing temperatures are kept below the glass transition temperatures of the organic layers within the structure. Furthermore, in-plane stress build up, can be relaxed over time, which means that crack-free sandwich layers containing inorganic and organic layers can be obtained. Another important point is to assure adequate adhesion between the different layers of the inorganic-organic structure. This can be difficult to achieve in some cases, but with the use of adhesion promoters and/or specially designed surface treatments, as described herein, this problem can be overcome.

Spin-on-glass (SOG) may be used to make the inorganic core layer of the waveguide structure. This is suitable because the spin-coating provides adequately smooth surfaces compared with evaporated or sputtered $SiO_2$ or e.g. $Si_xN_y$, and because from a manufacturing point of view, SOG makes the structure orders of magnitude cheaper and simpler to build compared to films fabricated using standard cleanroom deposition techniques. However, those methods can also be used if preferred.

All the layers comprising the structure will preferably have sufficiently low surface roughness (root mean square roughness<1 nm). This is a general criteria for all waveguides in order to minimize attenuation of the guided light. Low surface roughness is furthermore important for the current invention because smooth surfaces are important to obtain low background scattering and hence high signal-to-noise for weakly scattering objects. Surfaces with similar low roughness may be achieved if the core is made from a polymer, but core layers made of polymers offer fewer possibilities than inorganic materials when it comes to surface functionalization and in some cases, such as for PMMA, the organic layers are not chemically inert (i.e. they cannot be used together with certain solutions such as methanol, ethanol etc.).

SOG comes in different forms and in different solvents, but generally the hardening steps involves baking at temperatures exceeding 400° C. Such high temperatures cannot be applied for the present hybrid waveguide structure due to the inherent material property differences (see above). However, it has been realized that by baking the SOG layer at lower temperatures for extended times results in SOG films with very similar characteristics as SOG films cured for short time at high temperatures.

Using inorganic $SiO_2$ as core-layer instead of polymer is particularly beneficial in at least three aspects. First, the $SiO_2$ surface is very good from a surface chemistry point of view. One example is the formation of supported lipid bilayers, which typically is difficult to form on other substrates than $SiO_2$. A second reason is that $SiO_2$ is usually more chemically robust/inert than most polymers, meaning that organic solvents can be used for cleaning the waveguide surface and/or for preparing biological specimen to be measured. The third reason is because of its physical and chemical robustness: $SiO_2$ can form a natural etch-stop layer, making special protective measures during fabrication processing for protecting the core layer, for example during etching, unnecessary which again reduces processing time and complexity.

A main feature of the waveguide structure disclosed herein is that it combines an inorganic core with an organic cladding environment. This structure, and its method of production, was developed to (i) make the surface chemistry of the inorganic core compatible with e.g. lipid bilayer formation, silane-based chemistry, surface modifications based on electrostatic attraction, such as polylysine derivatives etc., (ii) use the organic cladding to match the refractive index of the sample medium, (iii) allow for an optically symmetric waveguide (which has been found being an advantage for coupling in light and for eliminating cut-off conditions for the fundamental mode) and (iv) to ensure low scattering as the evanescent field passes the cladding layer and enters the sample medium/liquid reservoir, i.e. the sample well arranged onto the inorganic core in the waveguide structure (which appears not to have been previously considered a critical aspect and thus an advantage with respect to high signal-to-noise if the detection/measurement system is operated in scattering mode).

The Cladding Layers

The waveguide structure may comprise two types of dielectric materials forming a three-layered structure. An inorganic high refractive index material forms the core layer of the structure while an organic polymer with a refractive index lower than that of the core layer forms the upper, and possibly also the lower, cladding layer. Thereby, it may define a symmetric cladding environment for the core layer. A symmetric cladding makes light in-coupling through butt-coupling easy (due to high modal overlap) and ensures that at least the fundamental mode is always supported by the structure for for all wavelengths (eliminates a cut-off thickness for the core layer for sustaining the fundamental mode). Symmetric waveguides have no cut-off for the fundamental mode of the waveguide. The refractive index of the polymer forming the upper cladding layer, which forms the walls around the sample well, should be as closely matched to that of the sampling medium as possible. For the case of water as sampling medium ($n \approx 1.33$), the difference between the refractive index of the cladding layer and the refractive index of water should preferably not be more than about 0.03 (i.e. $1.30 \leq n_{cladding} \leq 1.36$). This close index matching between the sampling medium and the upper cladding ensures low stray light scattering in the sample well. This is an important point if the waveguide structure is to be used for monitoring scattering intensity but not as important if it is to be used for monitoring fluorescence signal only. Not many materials have a refractive index closely matching that of water. Only a few, such as Teflon or Teflon-like polymers with refractive indices around $n=1.35$, appear to exist. An example is CYTOP, a fluorinated polymer from AGC Asahi Glass with $n=1.34$ at $\lambda=532$ nm. Another example is MY-133 MC from My Polymers Inc. with a refractive index close to 1.33 at $\lambda=589$ nm. Besides having the appropriate refractive indices, both these polymers show strong chemical resistance, both have high Abbe numbers and low autofluorescence. In many cases these Teflon-like polymers are extremely hydrophobic, making it difficult to fabricate layered structures with them. However, this adhesion problem can be solved by depositing a thin layer of aluminium on the hydrophobic polymer surface and subsequently removing it by wet etching in a basic solution such as sodium hydroxide. This treatment makes the polymer sufficiently hydrophilic to ensure good adhesion between it and a subsequently casted or deposited (inorganic or organic) material.

The Core Layer

In principle the core layer can be made from any optically transparent material of choice, as long as its refractive index is larger than that of the cladding layers. The penetration depth of the evanescent field of the guided mode will be determined by the waveguide layer properties, such as thicknesses and refractive indices. By tailoring these parameters, the penetration depth can be tuned from around 100 nm to more than 2-3 micrometers or even more. The core layer can be made as thin as desired but its thickness should preferably be smaller than the cut-off thickness for the higher order modes, since a single-mode behaviour is preferred. A single mode waveguide is a waveguide structure that only supports a single fundamental mode for a certain wavelength. A single mode waveguide is preferred since it a) ensures high modal overlap between the fundamental mode of the waveguide and the excitation source (the butt-coupled fiber), b) ensures an even and controlled illumination profile within the sample well, c) ensures better control of the penetration depth of the evanescent field, d) ensures high optical density within the waveguide, which is important for obtaining high enough scattering signal to be detected by a standard camera (microscope or other) or photodetector.

A core layer made of glass ($SiO_2$) such as SOG is preferable when working with biological systems since most surface chemistries used are designed for such surfaces. In order to reduce stray light scattering and waveguide attenuation, the core layer has to be as flat as possible, the flatter the better. Root means square roughness should preferably not exceed 1 nm. Inorganic $SiO_2$ is ideal for surface carrying out various functionalisation schemes.

BRIEF DESCRIPTION OF DRAWINGS

In the description of the invention given below reference is made to the following figure, in which.

DETAILED DESCRIPTION

Figure 1A:
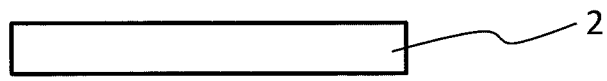
FIGS. 1a-j show an example of the method for manufacturing a waveguide structure.

The waveguide structure, the method of manufacturing such waveguide structure, and measurement systems comprising such waveguide structure will be described with reference to the accompanying drawings, in which example embodiments are shown. However, the waveguide structure, methods of manufacturing, and the measurement systems are not limited by the embodiments and examples described below and illustrated by the figures.

FIGS. 1a-1j schematically show an example of the method for manufacturing a waveguide structure 1. The fabrication process, i.e. the method for manufacturing the waveguide structure 1, should be carried out in a cleanroom facility, preferably ISO 100-1000 class. The waveguide structure 1 comprises three sandwiched layers 3, 4, 5 fabricated and patterned on a substrate 2—an optically flat supporting layer of choice, such as glass or Si wafers. In principle, any material can be used as substrate 2 as long as sufficient adhesion can be assured between it and the waveguide structure 1. The fabrication process comprises in this example nine steps as outlined in FIG. 1*a*-1*i*:

1*a*) Substrate 2 preparation.
1*b*) Spinning of lower cladding layer 4 and first aluminium layer 31 deposition and removal.
1*c*) Deposition of core layer 3.
1*d*) Spinning of upper cladding layer 5.
1*e*) Second aluminium layer 32 deposition and removal.
1*f*) Spinning of an etch mask 33.
1*g*) Lithography.
1*h*) Etching of a sample well 6.
1*i*) Dicing and removal of etch mask 33.

By this method, one or several waveguide structures may be manufactured simultaneously on one Si wafer. The resulting structures may be subsequently separated into individual waveguide structures by means of wafer dicing.

Figure 1B:
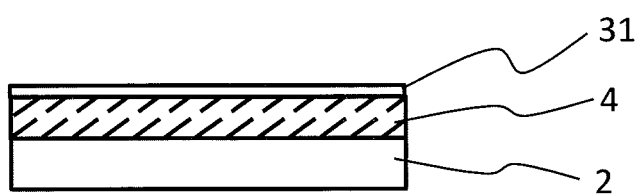
Figure 1C:
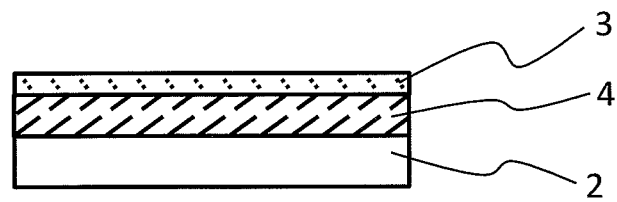
Figure 1D:
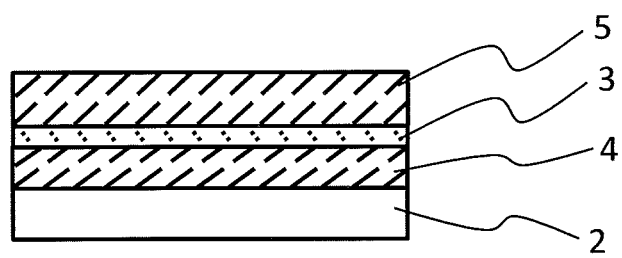
Figure 1E:
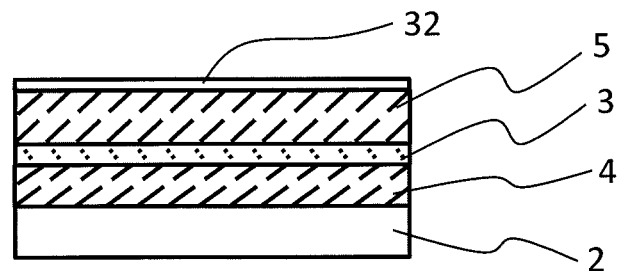
Figure 1F:
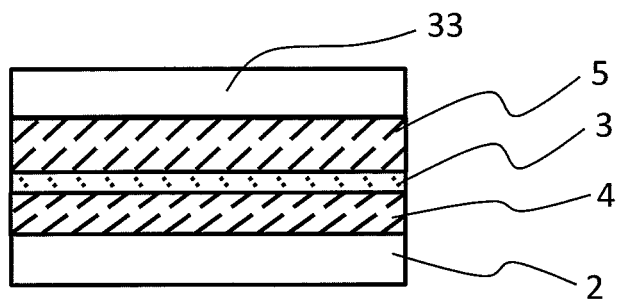
Figure 1G:
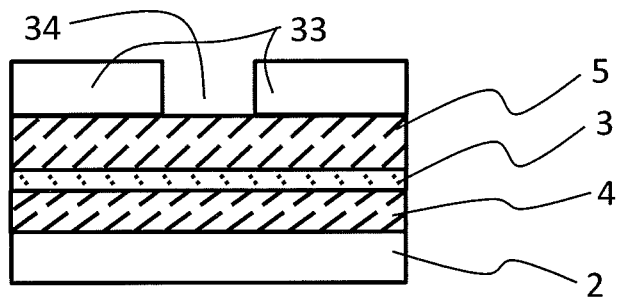
Figure 1H:
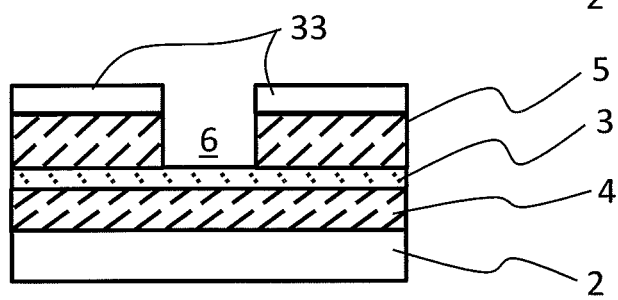
Figure 1I:
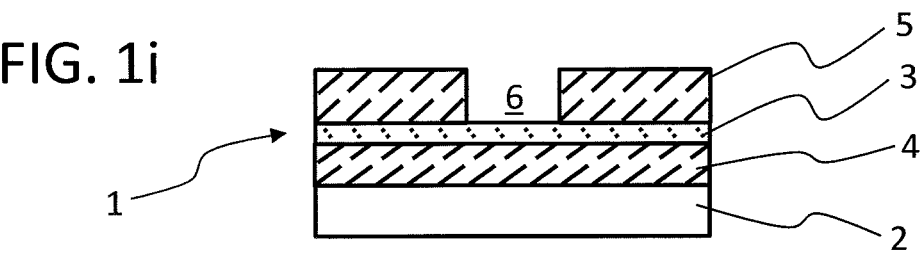
Figure 1J:
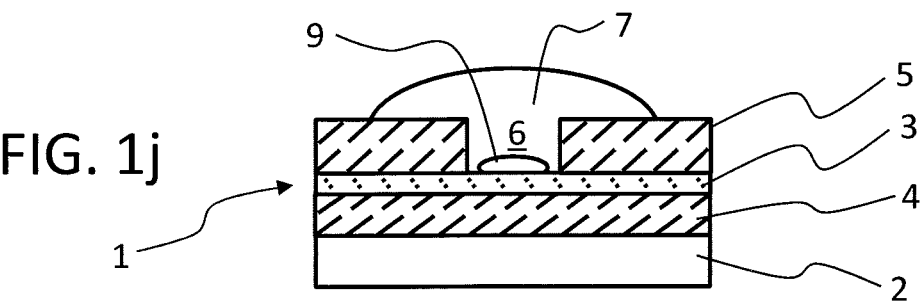

FIG. 1*j* shows a complete waveguide platform with a sample object 9, for example a biological specimen, in a sample medium 7, e.g. water, placed in the sample well 6 of the waveguide structure 1.

Substrate

A substrate 2 in the form of a homogenous flat support surface helps minimize losses in the waveguide since any surface irregularities, contamination or debris is likely to cause structural defects in the final structure which can affect the performance of the waveguide structure 1. Substrate cleaning, such as plasma ashing, may be necessary to help rid the surface of contamination prior to spinning of the lower cladding layer 4. Furthermore, hotplate baking at 200° C. for a few minutes may help remove water from the wafers surface which may help to improve adhesion between the surface of the supporting substrate 2 and the waveguide structure 1. Adhesion promoters can also be used to improve adhesion properties. In the case when a polished 4 inch Si(100) wafer is used as support layer and CYTOP as cladding layer 4, 5, an adhesion promoter has to be used to ensure adequate adhesion to the substrate 2. In this case, AP3000 and SIGMA-ALDRICH (3-Aminopropyl)triethoxysilane primes can be used as coupling agent to promote the CYTOP to silicon adhesion. The AP3000 primer is designed to be used with BBC polymer but works well with CYTOP as well. However, if the waveguide structure 1 is to be fabricated on a glass substrate 2 a different adhesion promoter has to be used. The promoter is spin-coated at around 4000 rpm for 30 seconds and let to dry in air at 60° C. for one minute.

Lower Cladding Layer

After priming, a lower cladding layer 3 is spin-coated on the substrate 2 in the desired thickness as shown in FIG. 1*b*. The lower cladding layer 4 has to be sufficiently thick so that the guided mode of the waveguide does not interact with the underlying substrate 2. In principle there is no upper limit for how thick the lower cladding layer 4 can be. After spin-coating, the lower cladding layer 4 should be cured or hardened according to specifications from the manufacturer. In case the lower cladding layer 4 is made of CYTOP, a convection oven should be used for hardening the polymer in a three-step baking process. First the CYTOP is brought into a 50° C. oven and prebaked at that temperature for one hour to remove gas and bubbles in the resin. After one hour the temperature should be increased to 80° C. at a ramping speed of 8° C./5 min and kept at 80° C. for an hour. The purpose of this step is to remove solvents from the layer. Drying occurs from the resin surface. After one hour the temperature should be raised to 250° C. at a ramping speed of 8° C./5 min and kept at that temperature for about two hours. The purpose of this step is to improve adhesion with the supporting material. Different cladding layer materials may require different baking/hardening procedures. During baking, a glass cover should be placed over the wafer in order to increase the film flatness and to help avoid particle contamination during the extended baking process.

CYTOP is naturally hydrophobic which makes subsequent film-coating difficult or even impossible. In order to overcome this problem a thin first aluminium layer 31 (or a layer of some other suitable metal) should be deposited as a film on the hardened CYTOP layer and subsequently removed using a solution of sodium hydroxide (or ma-D331, photoresist developer from Micro Resist Technology GmbH). The first aluminium layer 31 could be replaced by a layer of any other suitable metal or other material. After removing the first aluminium layer 31, the wafer should be rinsed thoroughly in deionized water and subsequently blow dried using filtered nitrogen. This treatment leaves the CYTOP surface less hydrophobic, which makes the subsequent core layer 3 adhere better to it.

Core Layer

Figure 2:
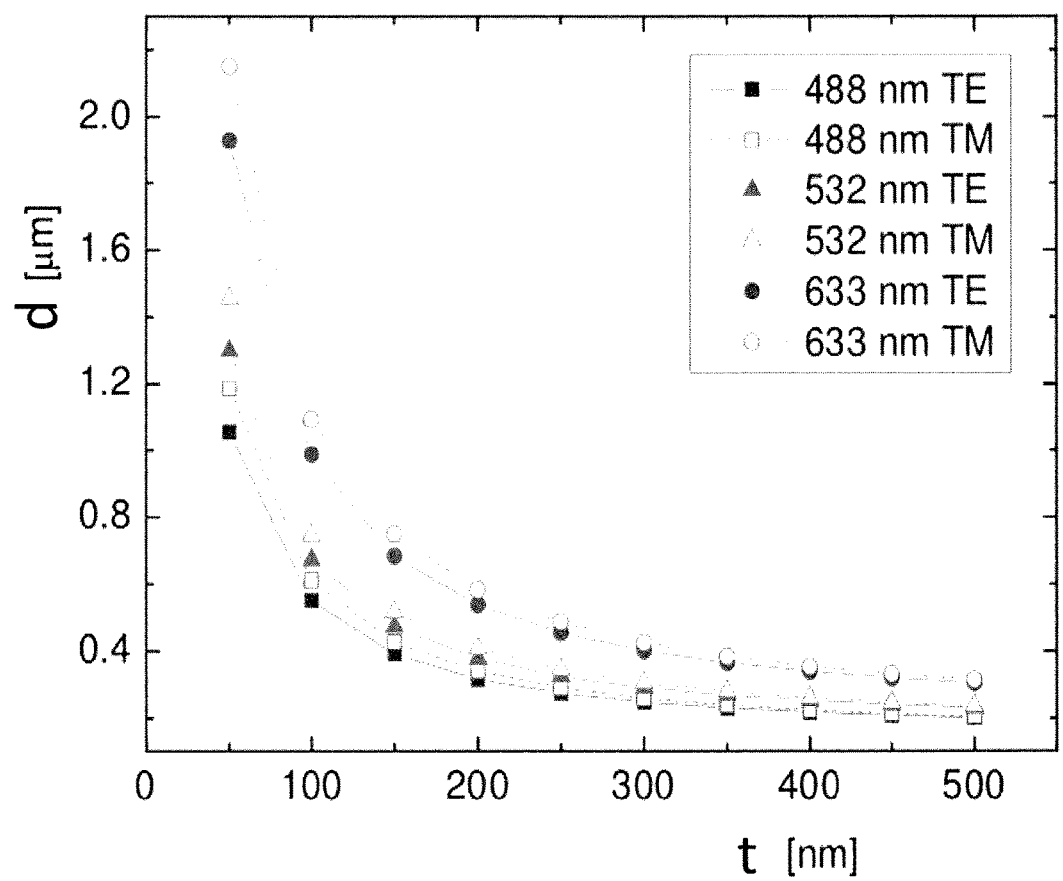
FIG. 2 shows penetration depth of the evanescent field as a function of SOG core layer thickness for some commonly used wavelengths and two polarizations.

The core layer 3 can in principle be made of any optically transparent material with refractive index higher than that of the surrounding cladding layers 4, 5. However, the fabrication of the core layer 3 cannot involve heating to temperatures above the glass-transition temperature of the cladding layers 4, 5. In the case of CYTOP, this temperature is around 120° C. The core layer 3 can be deposited with chemical vapor deposition, sputtering, thermal evaporation (resistive or e-beam) or any other standard cleanroom deposition method. It can also be simply spin-coated on top of the lower cladding layer 4 and hardened appropriately. In the case when CYTOP is used as lower cladding layer 4 and SOG as core layer 3, the SOG film is preferably spin-coated on top of the lower cladding layer 4 in the desired thickness and hardened in a vacuum conduction oven at 120° C. for a time exceeding 24 hours. The core layer 3 having been applied on top of the lower cladding layer 4 is shown in FIG. 1*c*. The vacuum oven baking ensures strong solvent evaporation and results in a very flat surface, which is necessary in order for the resulting waveguide structure 1 to have good optical characteristics, for example low stray light scattering (background scattering) and attenuation. By varying the core layer 3 thickness it is possible to tailor the penetration depth of the evanescent field of the waveguide platform. FIG. 2 shows a graph of the calculated penetration depth d of the evanescent field as a function of the thickness t of a SOG core layer 3 with CYTOP cladding layers 4, 5 for some commonly used wavelengths for light in transverse electric TE and transverse magnetic TM polarized states.

Upper Cladding Layer

The last structural layer of the waveguide structure is the upper cladding layer 5. A sample well 6 will then have to be made into this layer in order to expose the core layer 3 to media to be analysed. In this example, the upper cladding layer 5 is directly spin-coated on the core layer 3 (FIG. 1*d*) and processed accordingly, but not in a way that involves heating to temperatures exceeding the glass transition temperature of the cladding material. In the case when CYTOP is used as cladding layers 4, 5, a vacuum thermal conduction oven is preferably used for hardening the CYTOP. The wafer is preferably placed in the oven at 50° C. and kept at that temperature for 30 minutes in order to remove gas and bubbles from the resin. After 30 minutes, the temperature should be increased to 80° C. at a ramping speed of 8° C./5 min and left at that temperature for 30 minutes. This step is for removing solvents from the upper cladding layer 5. After 30 minutes, the temperature is further increased to 100° C. at a ramping speed of 8° C./5 min and kept at that temperature for one hour before being allowed to naturally cool down to room temperature inside the vacuum oven.

Second Aluminium Layer

In order to define a sample well 6 in the upper cladding layer 5, a layer of resist (e.g. photoresist, e-beam resist) is placed on the upper cladding layer 5 and patterned accordingly. In the case CYTOP is used as upper cladding layer 5, it will first have to be made hydrophilic to ensure good adhesion of the resist layer. For this a 20-30 nm thick second aluminium layer 32 is deposited onto the surface of the upper cladding layer 5, see FIG. 1e, using for example e-beam evaporation and subsequently removed by placing the wafer in a sodium-hydroxide rich ma-D331 developer for 2 minutes, and thereafter in deionised water for approximately 1 minute before being blow dried using nitrogen. The second aluminium layer 32 could be replaced by a layer of any other suitable metal or other material that transforms CYTOP from hydrophobic to hydrophilic.

Etching

The next step is to form an etch mask 33 on the upper cladding layer 5, see FIG. 1f. The form of the etch mask 33 can be of any size and shape and made of either standard photoresist, e-beam resist, or metal. The etch mask 33 layer has to be sufficiently thick to be able to protect the underlying upper cladding layer 5 from being etched.

In the case CYTOP is used as upper cladding layer 5, a thin layer of photoresist can be spincoated on the CYTOP after it has been made hydrophilic. In order to create a hole 34 in the photoresist etch mask 33 layer, a lithography mask defining the hole 34 is placed on top of the etch mask layer 33 before exposing the etch mask 33 to ultra violet light. Afterwards, the wafer is placed in an appropriate developer and then rinsed in deionized water and finally blow-dried using nitrogen. This leaves the upper CYTOP layer partially exposed as indicated in FIG. 1g. The hole 34 in the etch mask 33 will define the size and shape of the sample well 6 of the waveguide structure. The sample well 6 can be patterned in any desired way. Reactive-ion etching (RIE) is then applied to etch through the exposed CYTOP layer to form the waveguide sample well 6 (FIG. 1h) as a cut-out in the upper cladding layer 5. The sample well may be formed as follows. First a clean $O_2$ plasma is used to etch the first micrometer or so of the CYTOP. After that a 50/50 mixture of $Ar/O_2$ is used to etch the next three micrometers or so. Argon is chemically inert which means that its plasma sputters away undesired fragments and inorganic materials that can be found within the sample well 6 during etching. The final micrometer of CYTOP is then etched using a clean $O_2$ plasma to best protect the SOG core layer 3, in the sample well 6. In order to achieve as anisotropic etching as possible, chamber pressure should be kept at a minimum. Since etching rates vary between different etching systems, a thorough etching calibration should be performed to obtain the etching rates for cladding layer and the resist or metal used as etch mask 33 layer. In the exemplified case etching was carried out at 100 W for about 2+8+2 minutes at 30 mTorr with oxygen and argon at 40 sccm (standard cubic centimeters per minute). After RIE, the surface of the wafer, especially the exposed core layer 3, is highly reactive. In order to neutralize the surface, the wafer should be placed in deionized water for a few minutes, before being blow-dried using filtered nitrogen. The sample well 6 is thereby arranged on the upper side of core layer 3 and partially defined by cladding walls of the upper cladding layer.

Prior to wafer dicing, some photoresist or other suitable material of choice can be spun on the wafer to protect the structure from dicing debris. Dicing can be carried out using standard wafer dicing machines. The facets of the resulting chips will have to be of high enough quality in order for end-fire coupling of light into the core layer 3 to be efficient. The result will depend on type of dicing blade used, spin-speed and feeding rate.

Following the dicing of the wafer, the protecting layer and mask layer are removed using appropriate methods such as bathing in photoresist remover and/or metallic wet-etching solutions (see FIG. 1i).

Figure 3:
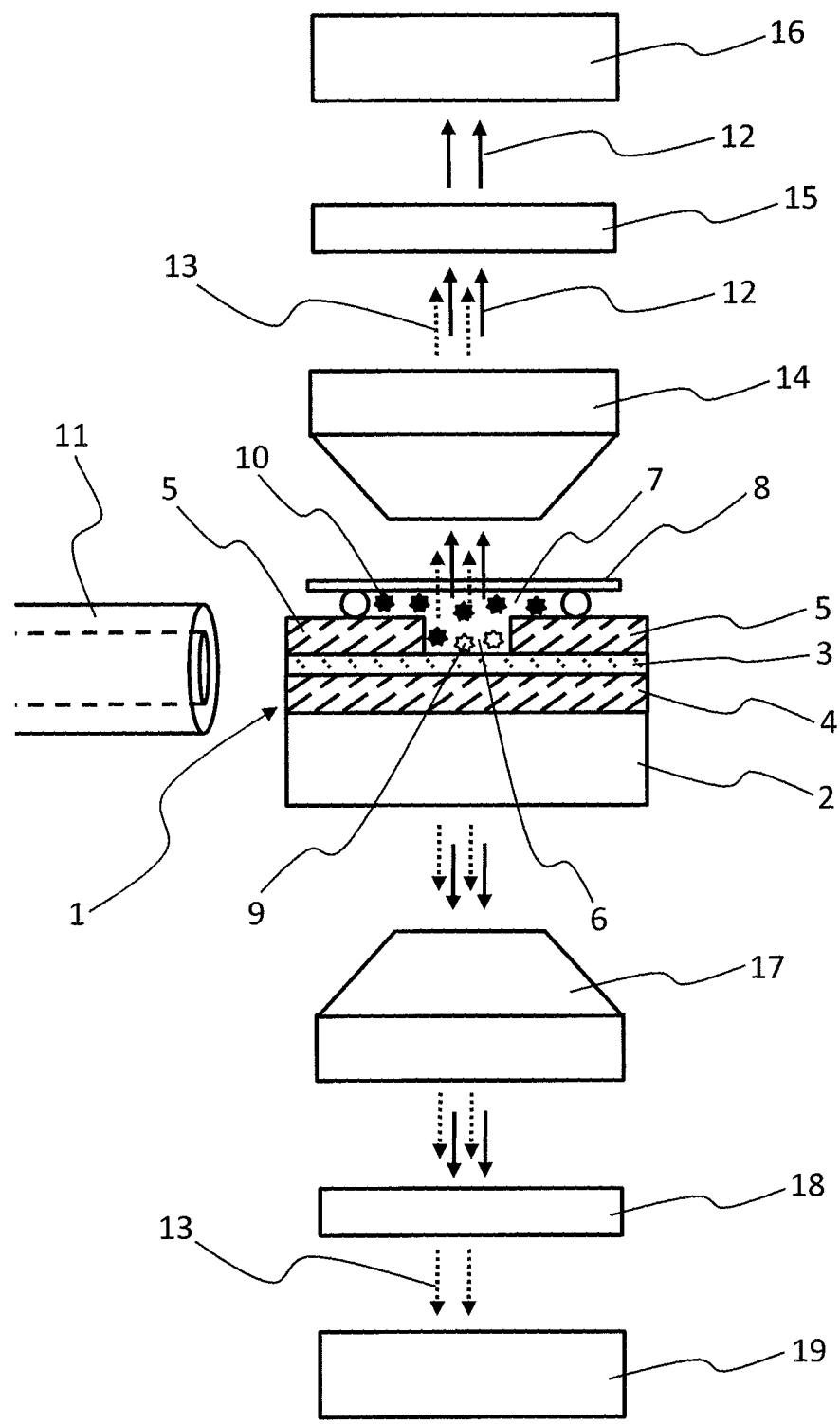
FIG. 3 shows a schematic overview of a first example of a measurement system comprising the waveguide structure.
Figure 4:
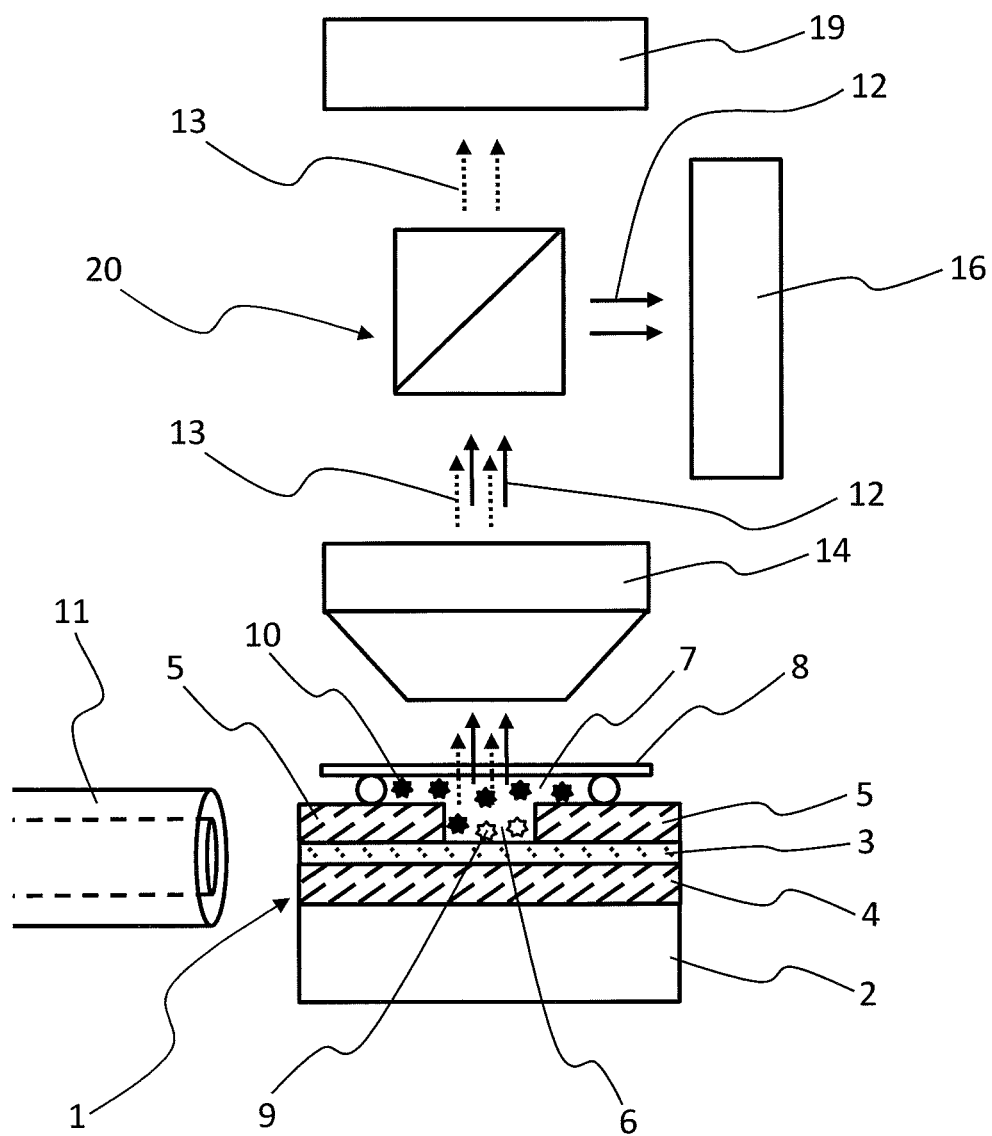
FIG. 4 shows a schematic overview of a second example of a measurement system comprising the waveguide structure.

FIGS. 3 and 4 show examples of measurement systems for e.g. label-free detection of nano- and microscopic objects. Both measurement systems comprise a waveguide structure 1, which may have been manufactured using the method described with reference to FIGS. 1a-1j. All optical signals originating from sample objects under examination can be detected simultaneously using various configurations, examples of which are given in FIGS. 3 and 4.

The measurement system in FIG. 3 comprises a waveguide structure 1. The waveguide structure 1 comprises a core layer 3, a lower cladding layer 4, and an upper cladding layer 5 upon a substrate 2. The waveguide structure, especially the core layer 3 and the cladding layers 4, 5, may comprise one or more of the features described in the summary section above. The waveguide structure may be a waveguide structure fabricated as described above with reference to FIG. 1a-1j. Sample objects 9, 10 such as lipid vesicles, metallic particles, biological cells, bacteria, viruses or molecules may be placed in a sample medium 7, such as water or other liquid, in the sample well 6 arranged on the upper side of the core layer 3 of the waveguide structure 1. The sample medium 7 can be held in place by an optically transparent plate 8 sealed to the waveguide structure 1 in a microfluidic type configuration. Input light from a light source, such as a laser, is fed from the side into the core layer 3, preferably via a butt-coupled optical fibre 11. When input light is guided into the waveguide structure 1, an evanescent wave is formed at the outer boundaries of the core layer 3. The penetration depth of the evanescent wave into sample well 6 is well defined, and hence the evanescent wave interacts only with sample objects 9 within its reach while more distant sample objects 10 are left unaffected, which results in a high signal to background ratio. Sample objects 9 placed within the penetration depth of the evanescent wave interact with the confined light and either scatter the light or absorb the light which can result in for example fluorescence or emittance of infrared radiation which can be easily detected. In the case that the sample objects 9 under examination are fluorescent, both fluorescence signals 12 and scattering signals 13 are produced more or less simultaneously. In upward direction, the signals 12, 13 emanating from the waveguide structure may be collected by a first objective 14. The scattering signals 13 may be filtered out by a first filter 15, such that only fluorescence signals 12 reach and are detected by a first detector 16. In downward direction, the signals 12, 13 emanating from the sample objects 9 due to interaction with the evanescent wave of the waveguide structure 1 may be collected by a second objective 17. The fluorescence signals 12 may be filtered out by a second filter 18, such that only scattering signals 13 reach and get detected by a second detector 19. Such an arrangement allows for both fluorescence and scattering signals 12, 13 to be measured simultaneously.

FIG. 4 also shows an example of a measurement system that can detect fluorescence signals 12 and scattering signals 13 simultaneously. The waveguide structure 1 and the light input of this measurement system are similar to that in FIG. 3. The difference lies in the separation of fluorescence and scattering signals 12, 13. The measurement system shown in FIG. 4 uses only a first objective 14 for collecting signals emanating from the waveguide structure. The fluorescence signals 12 and the scattering signals 13 are then separated by a dichroic mirror 20 before being detected by a first detector 16 and a second detector 19 respectively. The detectors 16, 19 may be arranged with filters filtering out the scattering or fluorescence signals 13, 12 respectively.

The input light source and the detectors 16, 19 of the measurement systems in FIGS. 3 and 4 may be controlled by a control unit such as a computer.

Figure 5:
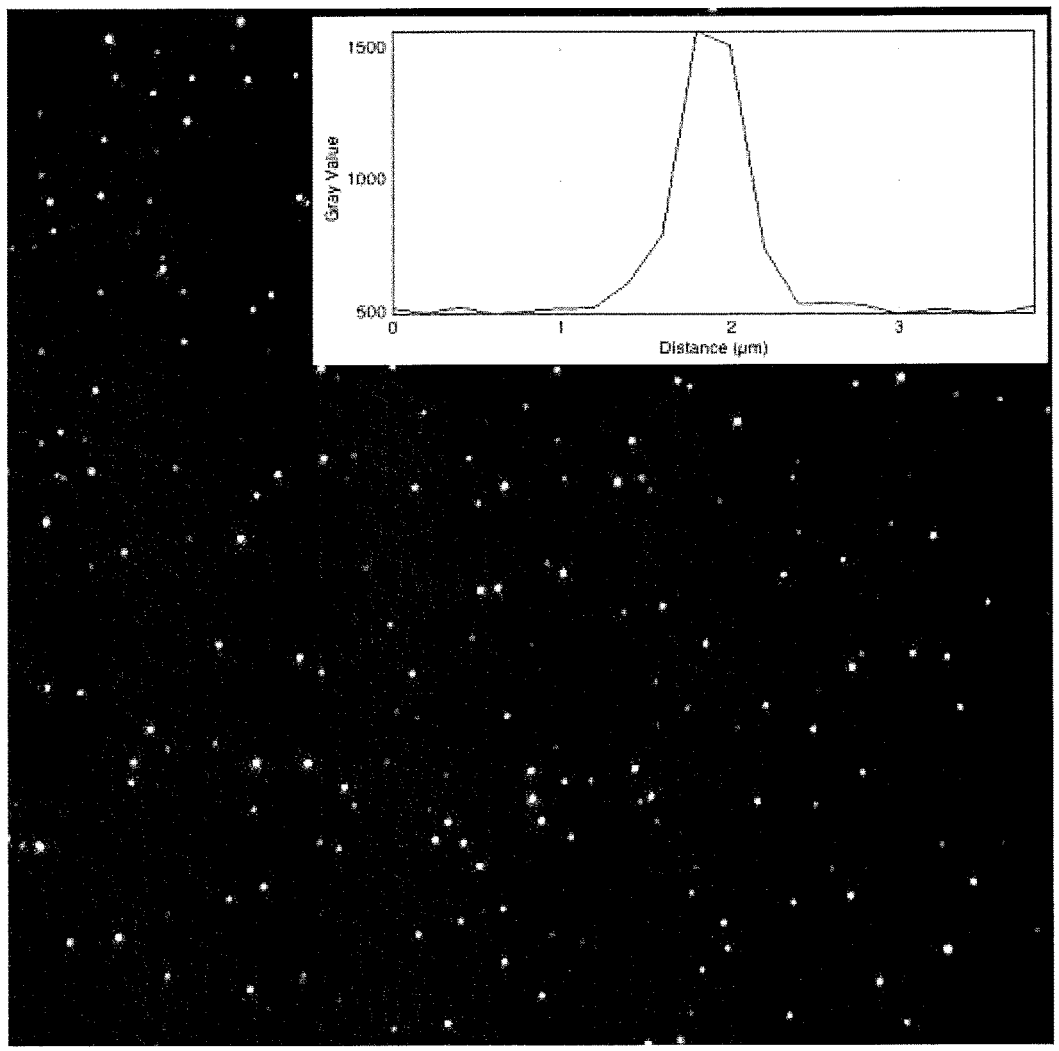
FIG. 5 shows the scattering intensity obtained in bright field of 30 nm gold nanoparticles adsorbed on a SOG core layer of the waveguide structure. The inset shows a typical intensity profile of a single 30 nm gold nano particle.
Figure 6:
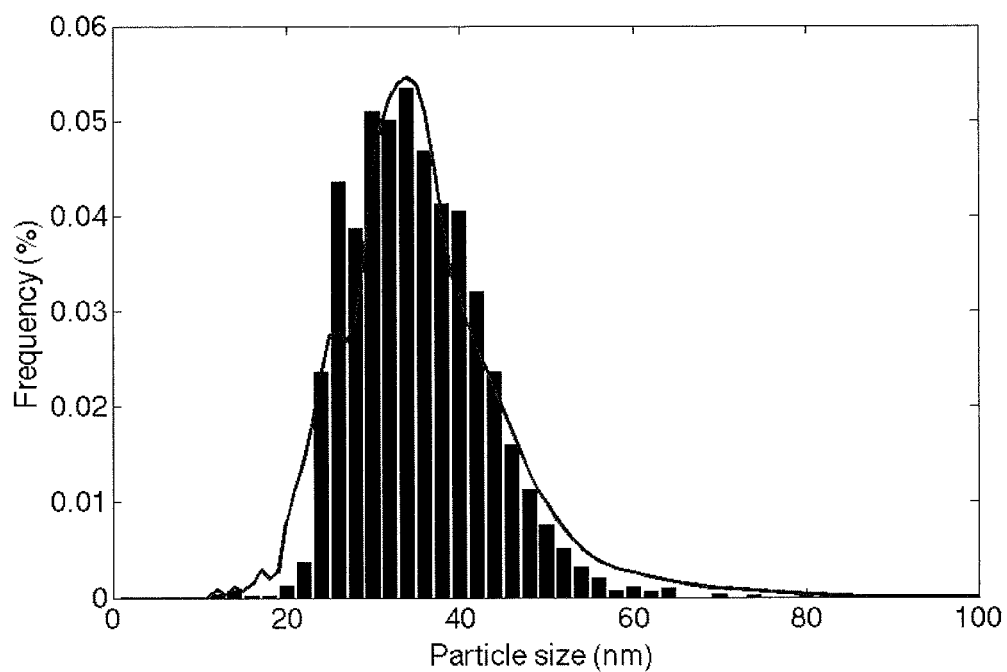
FIG. 6 shows the size distribution of the adsorbed 30 nm gold nanoparticles of FIG. 5.
Figure 7:
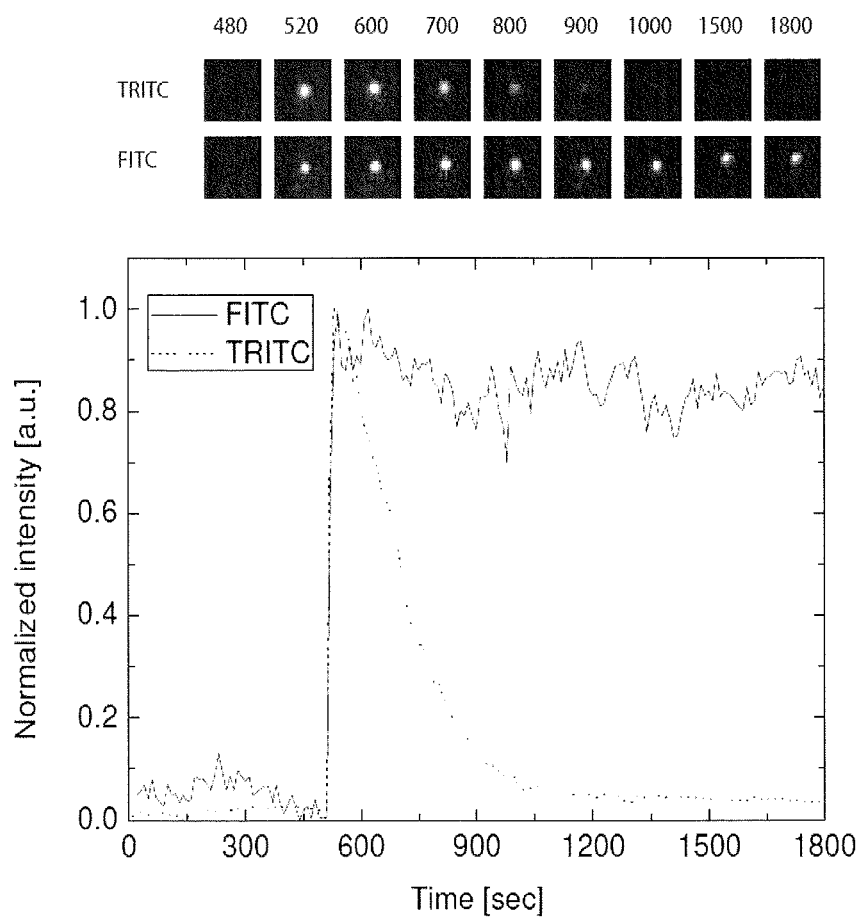
FIG. 7 shows the detected scattering and fluorescence emission intensity versus time for an adsorbed lipid vesicles with a diameter of around 100 nm being modified with 1% rhodamine labeled lipids.

FIGS. 5, 6, and 7 show the use of the waveguide structure to detect adsorption of metal, dielectric and fluorescently labelled nanoparticles to the core layer of the waveguide. The examples serve to more fully describe the manner of using the waveguide structure and to set forth the best modes contemplated for carrying out various aspects of the disclosure. It is understood that these examples in no way limit the true scope of this disclosure, but rather are presented for illustrative purposes.

FIG. 5 shows a 200×200 μm$^2$ bright field image of 30 nm gold nano particles absorbed on the SOG core layer of the waveguide structure. The image is obtained using a 40λ, N.A.=0.75 objective and a EM-CCD camera set to 10 ms exposure and gain=100 (Andor Luca EMCCD). A fiber-coupled 532 nm laser (NANO 250 Qloptiq, 532 nm) was used for coupling a TE polarized light into the waveguide. The power of the laser was set to 10 mW, but only a fraction of that power was actually coupled into the waveguide. The inset shows a typical intensity profile of a single 30 nm gold particle obtained using the waveguide indicating high signal-to-background and signal-to-noise ratios.

FIG. 6 shows how the intensity from multiple gold particles from one or multiple images, such as FIG. 5, can be combined and used to estimate the size distribution of adsorbed particles. The histogram shows the measured size distribution from >3000 gold nanoparticles with an average diameter of 30 nm on the waveguide. The solid line shows the corresponding size distribution obtained with a conventional nano particle tracking analysis (NTA) from the same particle batch in solution.

FIG. 7 shows the detected scattering and fluorescence emission intensity versus time for an adsorbed lipid vesicles with a diameter of around 100 nm being modified with 1% rhodamine labeled lipids. A fibercoupled 532 nm laser (NANO 250 Qloptiq, 532 nm) was used for coupling a TE polarized light into the waveguide. The scattering image is obtained using a FITC filter which filters out the fluorescence light. The fluorescent image is obtained using a TRITC filter which filters out the scattered light.

Additional examples (not shown in any figure) of measurements that may be performed using a measurement system as described above include:
(i) Time resolved detection of changes in scattering intensity and/or combination of scattering intensity and fluorescence emission upon binding to the surface of the core layer of metal nanoparticles, lipid vesicles or other nano- or micron-sized objects, such as quantum dots, polymers, virus particles, exosomes, platelets, live cells etc, carrying or being modified with a first probe molecule that either
  a) bind specifically to a target molecule which also binds specifically to a second probe molecule attached to the surface of the core layer of the waveguide or
  b) bind specifically to a target molecule attached to the surface of the core layer of the waveguide.
(ii) Detection of time resolved changes in scattering intensity and/or combination of scattering intensity and fluorescence emission of adsorbed metal nanoparticles, lipid vesicles or other nano- or micron-sized particles induced upon their interaction with biomolecules (DNA, peptides, proteins, e.g. enzymes, etc), metal nanoparticles, lipid vesicles or other nano- and micron-sized particles.
(iii) Detection of time resolved changes in position and scattering intensity of individual scattering and/or fluorescent objects in response to their motion within the evanescent field of the waveguide, and in particular the mobility of metal nanoparticles bound to the fluid lipid bilayer membrane of surface-attached lipid vesicles, supported lipid bilayers, exosomes, virus particles, platelets, live cells etc.
(iv) Detection of time resolved changes in scattering intensity and/or combination of scattering intensity and fluorescence emission upon structural changes of surface-bound nano- or micron-sized objects such as polymers, lipid vesicles, virus particles, exosomes, platelets, live cells etc., e.g. size fluctuations of lipid vesicles in response to varied osmotic pressure of the solution.

The waveguide structure, the method of manufacturing the waveguide structure, and the measurement system are not limited by the embodiments and examples described above but can be modified in various ways within the scope of the claims. For instance:

Incoupling

Even though symmetry of the waveguide structure makes incoupling of light directly through butt-coupling a very feasible option, the same effect can be obtained by other means of incoupling such as prism-incoupling or grating incoupling. These methods are generally not considered as straightforward and easy to apply as the butt-coupling scheme.

Incoupling can be carried out from more than one place simultaneously (incoupling from more than one side) in order to insure a more homogeneous illumination scheme.

Materials

The core layer can be replaced with other types of inorganic materials, such as $Si_xN_y$, or $Al_2O_3$, $TiO_2$ etc. which can either be deposited using standard deposition methods or spin coated. This can be useful for achieving different penetration depths or surface functionalizations. A waveguide constructed entirely out of either organic materials or inorganic materials alone will not have the same advantageous properties as the hybrid version when it comes to biocompatibility ($SiO_2$ core layer) or to reduce stray light scattering (cladding layer with matching refractive index to that of the sampling/probing medium).

Symmetry Vs. Asymmetry

Even though the symmetry of the waveguide structure ensures no cut-off for the fundamental mode and makes simple incoupling by butt-coupling possible, alternatively the waveguide may be asymmetric in the way that the lower cladding layer has a refractive index lower than that of the core layer and of the upper cladding layer. The upper cladding should however still be as closely index matched to the sampling/probing medium as possible, especially if the structure is intended for used with scattering signals. This asymmetric configuration will introduce a cut-off thickness below which no mode will be supported by the waveguide structure. This will also result in less modal overlap between the supported mode of the waveguide structure and the Gaussian shaped beam of the incoupled light, making incoupling less efficient. However, this configuration will increase the penetration depth of the evanescent part of the supported fundamental mode of the waveguide which can be beneficial in some applications.

Lightsource

Preferably a single transverse mode light source should be used (such as a laser), for most effective incoupling. However any other lightsource such as LED, white light halogen, mercury etc. can in principle be used. Multiple wavelengths can be used simultaneously (especially in the butt-coupling configuration) and the light source can even be incorporated directly into the waveguide platform for an in-chip light source type of configuration.

Additions

The waveguide structure and/or the measurement system may further comprise any type of microfluidic system to facilitate the transfer of fluids to and from the excitation the sample well of the waveguide structure.

The waveguide structure can be designed to work in combination with a plasmon polariton sub-unit.

The waveguide structure can be designed to work in combination with structured illumination thus enabling super resolution microscopy.

The waveguide structure can be designed to work as or in combination with optical tweezers by using the evanescent field to provide attractive or repulsive force to objects within the penetration depth.

The waveguide structure can be designed to have single or multiple sensing wells of various shapes and sizes enabling multi-well parallel readout possibilities.

The waveguide structure can be designed to work as a label-free sensor for sensing changes in refractive indices within the penetration depth of the evanescent wave realized due surface binding events in a Mach-Zehnder type of configuration. The Mach-Zehnder interferometer is well known to a person skilled in the art, and hence will not be further described here.

The sensing region of the waveguide, i.e. the surface of the core 3 which is exposed within the sample well, can be coated with a sufficiently transparent electrically conductive film, such as a conductive polymer, graphene, indium tin oxide, etc., to enable combined electrochemical analysis.

The invention claimed is:

1. A waveguide structure for evanescent wave microscopy and/or spectroscopy, comprising:
   an optically transparent core layer made of a first dielectric inorganic material;
   a lower dielectric cladding layer and an upper dielectric cladding layer arranged on opposite sides of the core layer, wherein the core layer has a refractive index higher than the refractive indices of the cladding layers, and wherein at least the upper cladding layer is made of an organic material, and wherein the root means square roughness of the upper surface of the core layer does not exceed 1 nm; and
   a sample well arranged on an upper surface of the core layer formed by a cavity in the upper cladding layer, wherein the sample well is adapted to contain a sample comprising a sample medium with one or more sample objects, wherein the upper cladding layer has a refractive index which closely matches the refractive index of the sample medium.

2. The waveguide structure of claim 1, wherein the lower cladding layer is made of an organic material.

3. The waveguide structure of claim 1, wherein the upper cladding layer is made of a fluorinated polymer.

4. The waveguide structure of claim 1, the refractive index of the upper cladding layer is within the interval 1.30-1.36.

5. The waveguide structure of claim 1, wherein the properties of the lower and upper cladding layers are similar such as to define a symmetric cladding environment for the core layer.

6. The waveguide structure of claim 1, wherein the core layer is made of $SiO_2$, $Si_xN_y$, $Al_2O_3$ or $TiO_2$.

7. The waveguide structure of claim 1, wherein the core layer is spin-coated onto the lower cladding layer.

8. The waveguide structure of claim 1, wherein the lower cladding layer is arranged on a substrate that supports the waveguide structure.

9. The waveguide structure of claim 1, wherein the waveguide structure is a single mode waveguide structure.

10. The waveguide structure of claim 1, wherein the surface of the core layer within the sample well is coated with an electrically conductive film having an optical transparency.

11. A measurement system, comprising:
    a waveguide structure, comprising:
    an optically transparent core layer made of a first dielectric inorganic material;
    a lower dielectric cladding layer and an upper dielectric cladding layer arranged on opposite sides of the core layer, wherein the core layer has a refractive index higher than the refractive indices of the cladding layers, and wherein each of the lower and upper cladding layers is made of an organic material, and wherein the root means square roughness of the upper surface of the core layer does not exceed 1 nm; and
    a sample well arranged on an upper surface of the core layer formed by a cavity in the upper cladding layer, wherein the sample well is adapted to contain a sample comprising a sample medium with one or more sample objects, and wherein the refractive index of the upper cladding layer of the waveguide structure deviates from the refractive index of the sample medium by 0.03 or less;
    at least one light source configured to direct light into the core layer of the waveguide structure towards the sample well; and
    a detector arrangement configured to detect light emitted from a sample comprising one or more sample objects in a sample medium placed in the sample well.

12. The measurement system of claim 11, wherein the at least one light source is butt-coupled to the core layer of the waveguide structure.

13. The measurement system of claim 11, wherein the at least one light source is a single transverse mode light source.

14. The measurement system of claim 11, wherein the detector arrangement comprises a first detector arranged to measure fluorescence signals emanating from the sample objects and a second detector arranged to measure scattering signals from the sample objects, such that fluorescence signals and scattering signals can be detected simultaneously.

15. The measurement system of claim 14, wherein a first filter is arranged to filter out scattering signals such that only fluorescence signals reach the first detector, and a second filter is arranged to filter out fluorescence signals such that only scattering signals reach the second detector.

16. The measurement system of claim 15, wherein a first objective is arranged between the waveguide structure and the first filter and a second objective is arranged between the waveguide structure and the second filter.

17. The measurement system of claim 14, wherein a dichroic mirror is arranged between the wave guide structure and the first and second detectors, wherein the dichroic mirror is arranged to separate fluorescence signals and scattering signals emanating from the sample objects such as to direct fluorescence signals toward the first detector and scattering signals toward the second detector.

18. The measurement system of claim 11, wherein the system is capable of detecting adsorption of metal, dielectric or fluorescently labelled nanoparticles to the core layer of the waveguide structure.

* * * * *